(12) United States Patent
Brice et al.

(10) Patent No.: US 8,242,276 B2
(45) Date of Patent: Aug. 14, 2012

(54) METHODS FOR THE PREPARATION OF N-(S)-1-AZABICYCLO[2.2.2]OCT-3-YL-1H-INDAZOLE-3-CARBOXAMIDE HYDROCHLORIDE SALT

(75) Inventors: Jodie Brice, Florence, SC (US); Miall Cedilote, Florence, SC (US); Zhiming Dong, Florence, SC (US); Pingsheng Zhang, Florence, SC (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/166,850

(22) Filed: Jun. 23, 2011

(65) Prior Publication Data

US 2012/0004412 A1 Jan. 5, 2012

Related U.S. Application Data

(60) Provisional application No. 61/359,844, filed on Jun. 30, 2010.

(51) Int. Cl.
*C07D 453/02* (2006.01)
(52) U.S. Cl. ...................................................... 546/133
(58) Field of Classification Search .................... 546/133
See application file for complete search history.

(56) References Cited

U.S. PATENT DOCUMENTS

2011/0172428 A1* 7/2011 Kuang et al. .................. 546/133

FOREIGN PATENT DOCUMENTS

| EP | 0469449 | 2/1992 |
| WO | 2004/029050 | 4/2004 |
| WO | 2005/063767 | 7/2005 |
| WO | 2005/092890 | 10/2005 |
| WO | 2005/111038 | 11/2005 |
| WO | 2006/001894 | 1/2006 |
| WO | 2006/069097 | 6/2006 |
| WO | 2007/038367 | 4/2007 |

OTHER PUBLICATIONS

Liu et al., "HCAPLUS: CAN 144:192261, AN 2006:135971, Preparation of Ionidamine".
Ferrari et al., "J. Heterocyclic Chem." 26:531-532 (1989).
"PCT International Search Report PCT/EP2011/050140—Issued Jan. 7, 2011."
Raffa et al., "Archiv der Pharmaize" 342:265-293 (2009).
Snyder et al., "J. Am. Chem. Soc." 74:2009-2012 (1952).
Smith et al., "Journal of Organic Chemistry" 23:621 (1958).
"English language abstract corresponding to STOLLE reference", (1924).
PCT International Search Report PCT/EP2011/060690—Issued Aug. 23, 2011.
Hwu et al., "Bioorganic & Medicinal Chemistry" 12:2509-2515 (2004).
Bermudez et al., "Journal of Medicinal Chemistry" 33:1924-1929 (1990).
Zhang, Yi, "HCAPLUS: CAN 142:430447, AN 2005:203871, Process for the Preparation of granisetron and its salt".
Stolle et al., "Chemische Berichte" 57:1123-1124 (1924).
Hou et al., "HCAPLUS: CAN 146:316842, AN 2006:770369—ISSN: 1001-5094, Study on synthetic route of ionidamine".
Xu et al., "HCAPLUS: CAN 135:19588, AN 2001:109038—ISSN: 1001-9677, Synthesis of indazole-3-carboxylic acid".
Lu et al., "Hcaplus: Can 149:332325, AN 2008:997937, Preparation of 1-benzoyl-indazole-3-carboxylic acid derivatives as contraceptives and/or antiviral agents".
Zhang et al., "Chinese Journal of Medicinal Chemistry" 16(6):366-368 (2006).

* cited by examiner

*Primary Examiner* — Binta Robinson
(74) *Attorney, Agent, or Firm* — George W. Johnston; Patricia S. Rocha-Tramaloni; Kimberly J. Prior

(57) ABSTRACT

The present invention provides novel methods for preparing N—(S)-1 -azabicyclo[2.2.2]oct-3-yl-1H-indazole-3-carboxamide HCl salt 1, a nicotinic α-7 receptor ligand, that are useful for the scaled-up preparation of compound 1. Compound 1 is useful in the treatment of disease conditions associated with defective or malfunctioning nicotinic acetylcholine receptors, especially of the brain, such as for the treatment of Alzheimer's disease and schizophrenia, as well as other psychiatric and neurological disorders.

14 Claims, No Drawings

METHODS FOR THE PREPARATION OF N-(S)-1-AZABICYCLO[2.2.2]OCT-3-YL-1H-INDAZOLE-3-CARBOXAMIDE HYDROCHLORIDE SALT

PRIORITY TO RELATED APPLICATIONS

This application claims the benefit of U.S. Provisional Application No. 61/359,844, filed Jun. 30, 2010, which is hereby incorporated by reference in its entirety.

FIELD OF THE INVENTION

The present invention provides novel methods for preparing N—(S)-1-azabicyclo[2.2.2]oct-3-yl-1H-indazole-3-carboxamide HCl salt 1, an agonist or partial agonist of the nicotinic α-7 receptor.

BACKGROUND OF THE INVENTION

Bicyclic indazole amides, such as N—(S)-1-Azabicyclo[2.2.2]oct-3-yl-1H-indazole-3-carboxamide HCl salt 1,

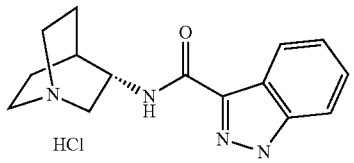

are described in WO 2004/029050, WO 2005/063767, WO 2005/092890, WO 2005/111038, WO 2006/001894, WO 2006/069097, and WO 2007/038367. These compounds are nicotinic α-7 receptor ligands. Compounds that act on the nicotinic α-7 receptor may be beneficial in the treatment of disease conditions associated with defective or malfunctioning nicotinic acetylcholine receptors, especially of the brain, such as for the treatment of Alzheimer's disease and schizophrenia, as well as other psychiatric and neurological disorders.

Indazole-3-carboxylic acid 3

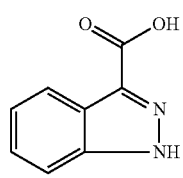

is a key starting material for the manufacture of compound 1.

To date, scale up reactions to prepare compound 1 safely and economically have not been successful. Accordingly, novel, efficient methods for preparing compound 1 on a scale up level are desirable.

SUMMARY OF THE INVENTION

The present invention, as illustrated in Scheme 1, provides a method for preparing compound 1:

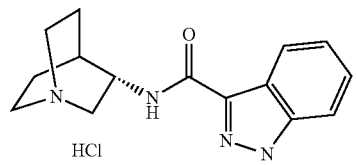

which comprises:
(a) reacting compound 3

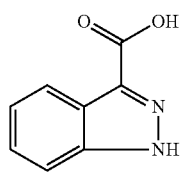

with thionyl chloride in an inert organic solvent to provide intermediate 4;

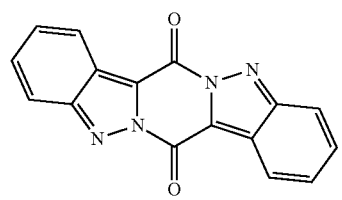

and
(b) reacting intermediate 4 with (S)-(−)-3-aminoquinuclidine dihydrochloride 5

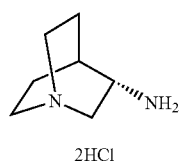

in an inert organic solvent in the presence of a non-nucleophilic base to form free base product 2,

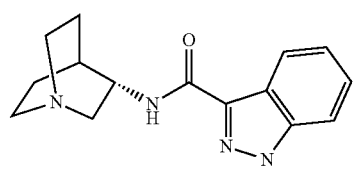

and acidifying free base product 2 with aqueous hydrochloric acid, to provide compound 1.

DETAILED DESCRIPTION OF THE INVENTION

As used herein, the following terms have the meanings set out below.

The term "inert organic solvent" refers to an organic solvent that does not interfere chemically with the reaction. Non-limiting illustrative examples of inert organic solvents include toluene, dichloromethane, chloroform, dimethylformamide (DMF), and the like.

The term "non-nucleophilic base" refers to an organic base that is a very strong base but is a poor nucleophile. Non-limiting illustrative examples of non-nucleophilic bases include triethylamine (TEA), N,N-diisopropylethylamine (DIPEA), 1,8-diazabicyloundec-7-ene (DBU), and the like.

The term "aqueous acidic solution" refers to solutions in which the solvent is water and the pH level is less than 7.0. The word "aqueous" means dissolved in water. An acid is any chemical compound that, when dissolved in water, gives a solution with a hydrogen ion activity greater than in pure water, i.e. a pH less than 7.0. Common examples of aqueous acidic solutions include acetic acid, hydrochloric acid (HCl), sulfuric acid, mixtures thereof, and the like, in water.

The term "free base form" refers to the pure basic form, generally of an amine, as opposed to its salt form. The amine may be an alkaloid and the free base form is commonly used to describe the unprotonated amine form of a compound. Many free base forms are unstable in their pure form and are often stored as salts. The salts usually exhibit greater water solubility. Common counterions include chloride, bromide, acetate and oxalate.

As set out above, the present invention provides a method for preparing compound 1:

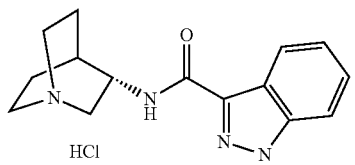

1

HCl which comprises:
(a) reacting compound 3

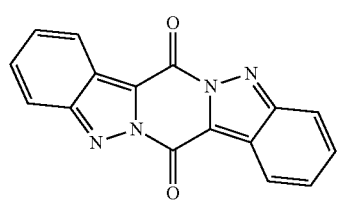

3 with thionyl chloride in an inert organic solvent to provide intermediate 4; and

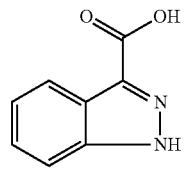

4

(b) reacting intermediate 4 from step (a) with (S)-(−)-3-aminoquinuclidine dihydrochloride 5

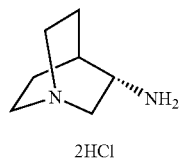

5

2HCl in an inert organic solvent in the presence of a non-nucleophilic base to form free base product 2,

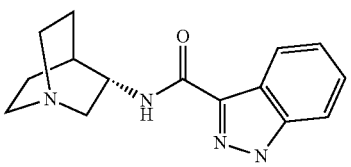

2 and acidifying free base product 2 with aqueous hydrochloric acid, to provide compound 1.

In one embodiment of the present invention, the inert organic solvent in step (a) is toluene.

In another embodiment of the present invention, step (a) is carried out at about 80° C., particularly about 60° C. to about 100° C., about 70° to about 90° C., about 75° C. to about 85° C., or at 80° C.

In another embodiment of the present invention, the inert organic solvent in step (b) is triethylamine.

In another embodiment of the present invention, step (b) is carried out at about 70° C., particularly at about 50° C. to about 90° C., about 60° C. to about 80° C., about 65° C. to about 75° C., or at 70° C.

In another embodiment of the present invention, compound 2 in step (b) is isolated by precipitation with water.

In another embodiment of the present invention, compound 1 in step (b) is isolated by precipitation with t-butyl methyl ether.

Another embodiment of the present invention relates to the preparation of N—(S)-1-azabicyclo[2.2.2]oct-3-yl-1H-indazole-3-carboxamide HCl salt.

The method of the present invention, as illustrated in Scheme 1, for preparing N—(S)-1-azabicyclo[2.2.2]oct-3-yl-1H-indazole-3-carboxamide HCl salt (1) from indazole-3-carboxylic acid 3, is set out below.

Scheme 1

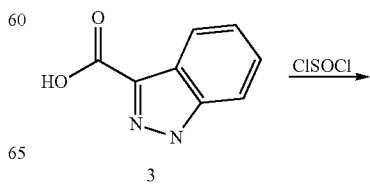

3

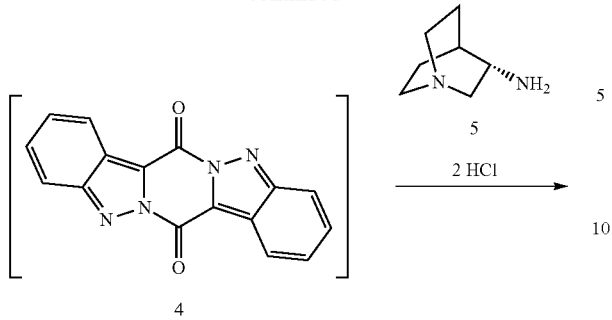

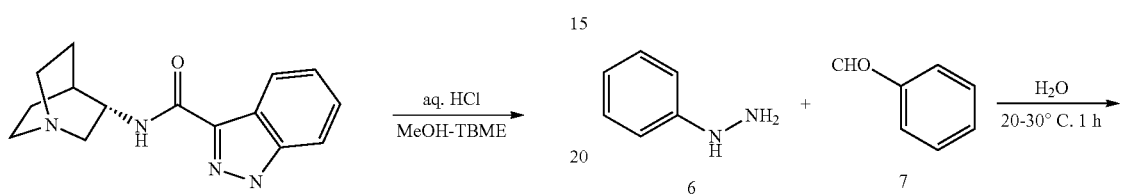

Compound 3 is converted to intermediate 4 by reacting 3 with thionyl chloride in an inert organic solvent, for example, toluene. This step is typically run in a temperature range of from about 40° C. to about 80° C., in particular at about 80° C. Upon the completion of the reaction, un-reacted thionyl chloride is removed, for example, by distillation from the system before initiating the second step. During distillation, toluene is also partially replaced with a different solvent that provides better solubility for 4 and 5. Many inert organic solvents that are inert to both compounds can be used, particularly N,N-dimethylformamide (DMF). Without isolation, crude 4 is reacted with (S)-(−)-3-aminoquinuclidine dihydrochloride 5 in the presence of a non-nucleophilic base, for example, tertiary amines, such as triethylamine (TEA), to provide free base product 2. Then the free base product 2 is acidified with aqueous hydrochloric acid to afford N—(S)-1-Azabicyclo[2.2.2]oct-3-yl-1H-indazole-3-carboxamide HCl salt 1. The method of the invention provides benefits over known methods, such as much lower cost and easier handling.

Compound 3 is first converted to intermediate 4, which is then reacted with the free base form of compound 5 to afford free base product 2. In the procedure, 5 is added together with 3 for operational convenience. During the conversion of 3 to 4, compound 5 is not reactive because it is in the disalt form. After the formation of 4, a base such as triethylamine (TEA) is added, which converts the disalt form of 5 to its free base form. The free-base form of 5 then reacts with intermediate 4 to produce free base product 2, which after acidification with aqueous hydrochloric acid provides compound 1.

The compounds of the present invention can be prepared according to the examples set out below. The examples are presented for purposes of demonstrating, but not limiting, the preparation of the compounds and compositions of this invention.

EXAMPLES

Example 1

Preparation of Indazole-3-carboxylic Acid (3)

Scheme 2

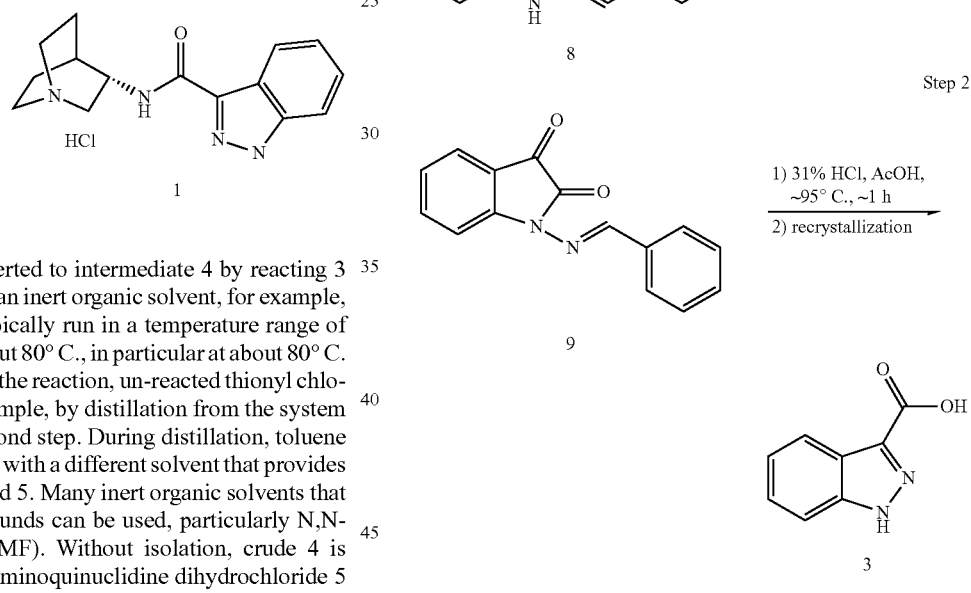

Step 1

A 5 L, half jacketed, 4-necked round bottom flask equipped with a mechanic stirrer, a thermocouple, and a nitrogen inlet, and an addition funnel, was charged with 322 g of phenylhydrazine 6 (2.98 Mol) and 3.3 L of water. Agitation was started. To the mixture was slowly charged 301 g of benzaldehyde 7 (2.84 Mol) in ~1 h, while maintaining batch temperature at 25-30° C. After the addition the mixture was stirred at 25-30° C. for at least 2 h and then cooled to 20° C. The solid was filtered, washed with 444 g of IPA. The wet cake was dried under vacuum at 70° C. overnight to give 540.4 g (97%) of benzaldehyde phenylhydrazone 8.

Step 2

A 3 L, half jacketed, 4-necked round bottom flask equipped with a mechanic stirrer, a thermocouple, a nitrogen inlet, and an addition funnel, was charged with 35.6 g of oxalyl chloride (280 mMol) and 200 mL of dichloromethane. The solution was heated to ~40° C. and a solution of 50 g of benzaldehyde phenylhydrazone (8) (255 mMol) in 800 mL of dichloromethane was added slowly. After the addition the mixture was stirred at ~40° C. for at least 2 h to generate intermediate solution I.

A second 3 L, half jacketed, 4-necked round bottom flask equipped with a mechanic stirrer, a thermocouple, a nitrogen inlet, and an addition funnel, was charged with 81.4 g of aluminum chloride (612 mMol) and 200 mL of dichloromethane. Agitation was started and the intermediate solution I in the first flask was slowly charged while maintaining batch temperature below 30° C. After the addition the mixture was refluxed for at least 2 h. The mixture was cooled to ~0° C. and 500 mL of water was slowly added while maintaining batch temperature <10° C. After the addition, the mixture was agitated for ~0.5 h. The agitation was stopped for layer separation. The bottom organic layer was separated. To the batch was added 100 mL of dichloromethane. The mixture was agitated for ~0.5 h. The agitation was stopped for layer separation. The bottom organic layer was separated. The combined organic solution was washed with 400 mL of 10% HCl, followed by 400 mL of brine. The organic solution was concentrated to dryness to give 60.1 g intermediate 9 (95%).

A 500 mL, half jacketed, 4-necked round bottom flask equipped with a mechanic stirrer, a thermocouple, and a nitrogen inlet, was charged with 28.7 g of intermediate (9) (115 mMol), 215 mL of acetic acid, 43 mL of water and 28.7 g of 31% HCl. The mixture was agitated at 90±5° C. for 1 h and then was concentrated to dryness. To the flask was added 300 mL of acetic acid. The mixture was agitated at 115° C. for ~0.5 h, cooled to ambient temperature under agitation, and was aged for at least 1 h. The solid was filtered, the wet cake was washed with 50 mL of acetic acid, dried under vacuum at 65° C. overnight to give 13.2 g (71% yield) of 3.

Example 2

Preparation of N—(S)-1-Azabicyclo[2.2.2]oct-3-yl-1H-indazole-3-carboxamide HCl Salt (1)

A 500 mL flask equipped with a mechanical stirrer, thermocouple, reflux/distillation setup and nitrogen inlet, was charged with 40.0 g of indazole-3-carboxylic acid 3, 54.0 g of (S)-(−)-3-aminoquinuclidine dihydrochloride 5, and 240 mL of toluene. The mixture was stirred at 20° C. to give a pale yellow slurry. To this slurry were added 4 drops of DMF and 44.0 g of thionyl chloride. The batch was heated at 80° C. for at least 4 h to finish the first step. Toluene and residual thionyl chloride were removed via vacuum distillation. To the mixture was added 100 mL of DMF. The batch was kept at ~70° C. while 74.9 g of triethylamine was charged. After the addition, the reaction was held at 70° C. and stirred for at least 4 hours. Upon the completion of the reaction, the mixture was cooled to 50° C. The mixture was distilled under reduced pressure to remove residual toluene. Once the distillation was complete, the mixture was kept at 60° C. and 51.7 g of 42% NaOH solution was added slowly (over ~5-10 minutes). The mixture was concentrated by vacuum distillation to remove TEA. The batch was diluted with 400 g of water to give an off-white slurry. The mixture was stirred at 60° C. for at least 1 hour and then cooled to 20° C. To the batch was slowly added 0-15 g of 31% HCl to adjust the pH to 9-10. The resulting slurry was stirred at 20° C. for 2 h and filtered. The filter cake was washed with 300 g of water (3×100 g), and dried under vacuum (>30 inch Hg) at 90° C. overnight to afford 88% yield of 2 as an off-white solid.

A 500 mL flask equipped with a mechanical stirrer, a thermocouple, and a nitrogen inlet was charged with 25 g of 2 and 69 g of methanol. Agitation was started, and the batch temperature was controlled at 20±5° C. After being agitated for about 30 minutes, the mixture was filtered through a Celite pad. The flask and the Celite pad were rinsed with 10 g of methanol. The combined filtrate was charged back to the flask and cooled to 5±5° C. To this solution was slowly added 26.1 g of 31% HCl, while maintaining the batch temperature at 5±5° C. After the addition, the mixture was stirred at this temperature for at least 1 h. A quantity of 147 g of t-butyl methyl ether (TBME) was added over 15 minutes. The slurry was then aged for at least 2 h. The solid was filtered, washed with 60 g of TBME, and dried under vacuum at 45±5° C. overnight to yield 24.7 g (87% yield) of compound 1.

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

We claim:

1. A method for preparing compound 1:

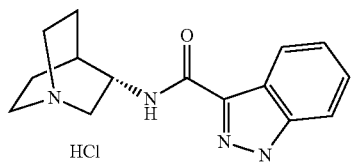

which comprises:
 (a) reacting compound 3

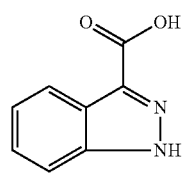

with thionyl chloride in an inert organic solvent to provide intermediate 4; and

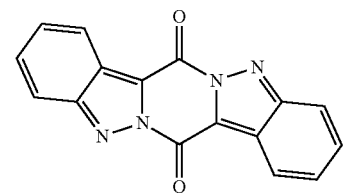

(b) reacting intermediate 4 from step (a) with (S)-(−)-3-aminoquinuclidine dihydrochloride 5

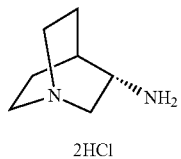

2HCl in an inert organic solvent in the presence of a non-nucleophilic base to form free base product 2,

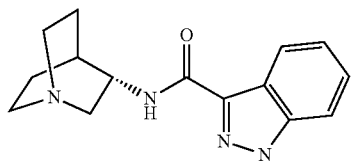

and acidifying free base product 2 with aqueous hydrochloric acid, to provide compound 1.

2. The method of claim 1, wherein the inert organic solvent in step (a) is toluene.

3. The method of claim 1, wherein step (a) is carried out at about 60° C. to about 100° C.

4. The method of claim 3, wherein step (a) is carried out at about 70° C. to about 90° C.

5. The method of claim 4, wherein step (a) is carried out at about 75° C. to about 85° C.

6. The method of claim 5, wherein step (a) is carried out at about 80° C.

7. The method of claim 1, wherein the inert organic solvent in step (b) is dimethylformamide.

8. The method of claim 1, where the non-nucleophilic base in step (b) is triethylamine.

9. The method of claim 1, wherein step (b) is carried out at about 50° C. to about 90° C.

10. The method of claim 9, wherein step (b) is carried out at about 60° C. to about 80° C.

11. The method of claim 10, wherein step (b) is carried out at about 65° C. to about 75° C.

12. The method of claim 11, wherein step (b) is carried out at about 70° C.

13. The method of claim 1, wherein compound 2 in step (b) is isolated by precipitation with water.

14. The method of claim 1, wherein compound 1 in step (b) is isolated by precipitation with t-butyl methyl ether.

* * * * *